United States Patent
Prisco et al.

(10) Patent No.: US 11,523,732 B2
(45) Date of Patent: Dec. 13, 2022

(54) SURGICAL DEVICE ACTUATED USING ASYMMETRIC SPRING SYSTEM

(71) Applicant: INTUITIVE SURGICAL OPERATIONS, INC., Sunnyvale, CA (US)

(72) Inventors: Giuseppe M. Prisco, Pisa (IT); Eugene F. Duval, Menlo Park, CA (US); Theodore W. Rogers, Alemeda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1141 days.

(21) Appl. No.: 16/117,935

(22) Filed: Aug. 30, 2018

(65) Prior Publication Data
US 2018/0368663 A1 Dec. 27, 2018

Related U.S. Application Data

(62) Division of application No. 12/494,797, filed on Jun. 30, 2009, now Pat. No. 10,080,482.

(51) Int. Cl.
*A61B 1/005* (2006.01)
*A61B 1/00* (2006.01)
(Continued)

(52) U.S. Cl.
CPC .......... *A61B 1/0052* (2013.01); *A61B 1/0016* (2013.01); *A61B 34/30* (2016.02); *A61B 2017/003* (2013.01); *A61B 2034/301* (2016.02); *A61B 2034/306* (2016.02); *A61B 2034/715* (2016.02)

(58) Field of Classification Search
None
See application file for complete search history.

(56) References Cited

U.S. PATENT DOCUMENTS 3,391,804 A 7/1968 Flatau
4,756,204 A 7/1988 Wittwer et al.
(Continued)

FOREIGN PATENT DOCUMENTS

CN 101115432 A 1/2008
CN 101327115 A 12/2008
JP 2004230189 A 8/2004

OTHER PUBLICATIONS

Extended European Search Report for Application No. 17175198.5, dated Aug. 29, 2017, 8 pages.
(Continued)

*Primary Examiner* — Manuel A Mendez
(74) *Attorney, Agent, or Firm* — Fish & Richardson P.C.

(57) ABSTRACT

A compliant surgical device such as a flexible entry guide employs tendons to operate or steer the device and attaches asymmetric or constant force spring systems to control tension in the tendons. As a result, the surgical device can be compliant and respond to external forces during a surgical procedure without rapidly springing back or otherwise causing a reaction that damages tissue. The compliance also permits manual positioning or shaping of the device during or before insertion for a surgical procedure without damaging the tendons or connections of the tendons within the device or to a backend mechanism.

20 Claims, 2 Drawing Sheets

(51) Int. Cl.
  *A61B 34/30* (2016.01)
  *A61B 17/00* (2006.01)
  *A61B 34/00* (2016.01)

(56) References Cited

U.S. PATENT DOCUMENTS

| | | |
|---|---|---|
| 4,768,762 A | 9/1988 | Lund |
| 5,415,158 A | 5/1995 | Barthel et al. |
| 5,650,704 A | 7/1997 | Pratt et al. |
| 6,272,371 B1 * | 8/2001 | Shlomo .................. A61B 5/065 |
| | | 128/899 |
| 6,477,396 B1 | 11/2002 | Mest et al. |
| 6,494,039 B2 | 12/2002 | Pratt et al. |
| 7,377,906 B2 * | 5/2008 | Selkee .............. A61M 25/0136 |
| | | 604/95.04 |
| 7,428,855 B2 | 9/2008 | Duval |
| 7,524,301 B2 | 4/2009 | Dubois et al. |
| 10,080,482 B2 | 9/2018 | Prisco et al. |
| 2001/0037051 A1 | 11/2001 | Fujii et al. |
| 2004/0010245 A1 * | 1/2004 | Cerier ................ A61B 17/0057 |
| | | 606/1 |
| 2004/0138700 A1 | 7/2004 | Cooper et al. |
| 2006/0015096 A1 | 1/2006 | Hauck et al. |
| 2006/0213305 A1 | 9/2006 | Sugar et al. |
| 2007/0156019 A1 | 7/2007 | Larkin et al. |
| 2007/0232858 A1 | 10/2007 | Macnamara et al. |
| 2008/0262480 A1 | 10/2008 | Stahler et al. |
| 2008/0277552 A1 | 11/2008 | Duval |
| 2008/0287862 A1 | 11/2008 | Weitzner et al. |
| 2009/0024141 A1 | 1/2009 | Stahler et al. |
| 2010/0094281 A1 | 4/2010 | Hauck et al. |

OTHER PUBLICATIONS

PCT/US10/38252 International Search Report and Written Opinion of the International Searching Authority, dated Sep. 24, 2010, 13 pages.

Robinson, David, William, "Design and Analysis of Series Elasticity in Closed-loop Actuator Force Control," Doctoral Dissertation in Mechanical Engineering, Massachusetts Institute of Technology, Jun. 2000, pp. 1-123.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

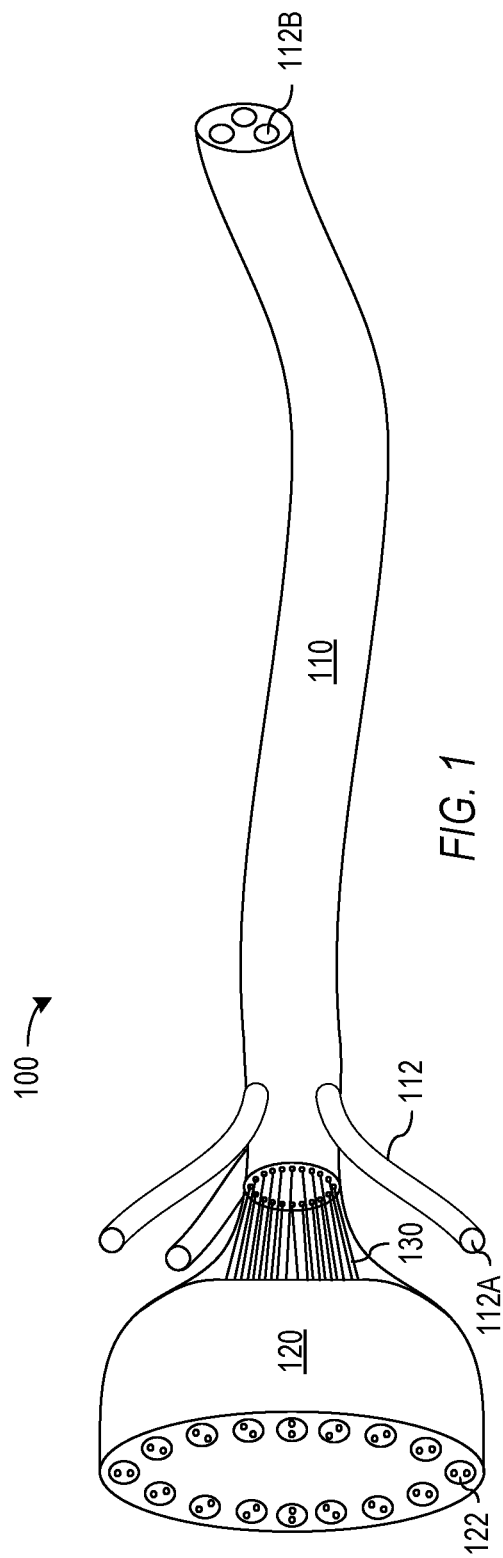
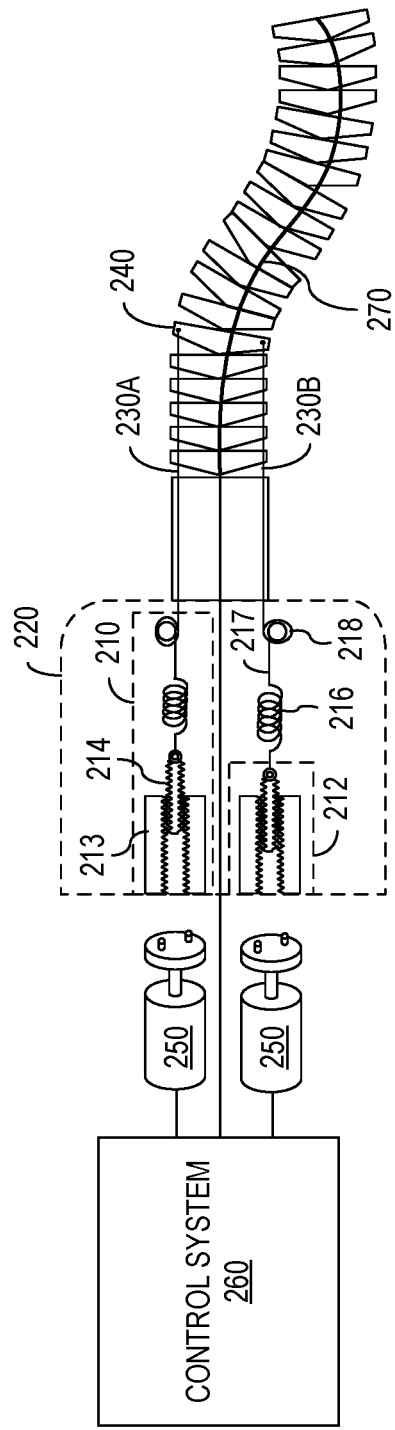
FIG. 1
FIG. 2A

SURGICAL DEVICE ACTUATED USING ASYMMETRIC SPRING SYSTEM

CROSS-REFERENCE TO RELATED APPLICATIONS

This patent document is a divisional of U.S. patent application Ser. No. 12/494,797, filed Jun. 30, 2009, which is hereby incorporated by reference in its entirety.

BACKGROUND

Minimally invasive surgical techniques generally attempt to perform surgical procedures while minimizing damage to healthy tissue. One particular technique for achieving this goal employs flexible surgical instruments that are able reach a target work site inside a patient by at least partially following a natural lumen such as the digestive tract of the patient. Following the natural lumen allows a surgeon to operate on the work site with less need for incisions made through healthy tissue, although an incision may be needed at locations where the flexible instrument enters or leaves a natural lumen. An entry guide can be used during such a surgical procedure to facilitate insertion and removal of surgical instruments or tools during the procedure. In general, the entry guide is inserted through an incision or a natural orifice and steered along a path to a point where the distal end of the entry guide nears or reaches a target work site. The entry guide generally contains one or more instrument lumens through which different surgical instruments can be inserted or removed. This allows instruments to be changed without requiring a delicate steering procedure each time a different set of instruments is needed.

Surgical instruments and entry guides that are able to follow a natural lumen or other convoluted paths generally must be flexible, which requires these devices to have properties and abilities that are not needed in most other surgical instruments. In particular, although an entry guide must be flexible enough to navigate a convoluted path, the guide ideally should provide a stable base at the work site for manipulation of an instrument or instruments inserted through the guide. Additionally, the guide should not change shape or react to external forces in a manner that could unintentionally damage adjacent tissue. Cables or tendons may extend through all or part of an entry guide for actuation of mechanical features of the entry guide or steering of the entry guide along its path. In some advanced surgical systems, these cables are robotically operated using motors and computer aided control. (As used herein, the terms "robot" or "robotically" and the like include teleoperation or telerobotic aspects.) The forces applied through the tendons can be significant, both to overcome friction and because the lengths of entry guides and instruments can create long moment arms. A flexible surgical device needs to control these relatively large forces so that reactions or movements along the length of the device do not damage the adjacent tissue of the patient.

SUMMARY

In accordance with an aspect of the invention, a compliant surgical device such as an articulated entry guide employs tendons to operate or steer the device and attaches constant force spring systems to control tension in the tendons. As a result, the surgical device can be compliant and respond to external forces during a surgical procedure without rapidly springing back or otherwise causing a reaction that damages tissue. The compliance also permits manual positioning or shaping of the device during or before insertion for a surgical procedure without damaging the tendons or connections of the tendons within the device or causing damage to a backend mechanism.

One specific embodiment of the invention is a surgical device such as an entry guide. The device includes a shaft having a movable member, a tendon attached to the member, a constant force spring system, and a control mechanism. The constant force spring system is attached to the tendon, and the control mechanism controls the magnitude that the constant force spring system applies to the tendon. The tension in the tendon can thus be independent of external forces moving the tendon but controlled to articulate the member.

Another embodiment of the invention is also a surgical device. This embodiment includes a shaft having a movable member, a tendon attached to the member, and an asymmetric spring system attached to the tendon. The asymmetric spring system is such that a force applied by the asymmetric spring system to the tendon has greater dependence on a location of a proximal end of the spring system than on a location of the tendon. A control mechanism can be connected to the proximal end of the asymmetric spring system.

Yet another embodiment of the invention is a method for operating a surgical device. The method includes inserting an articulated shaft of the surgical device for a surgical procedure, and using asymmetric or constant force spring systems to maintain balancing forces on members of the articulated shaft.

BRIEF DESCRIPTION OF THE DRAWINGS

FIG. 1 shows a flexible or articulated entry guide and backend mechanism in accordance with an embodiment of the invention.

FIG. 2A illustrates connections of two tendons to asymmetric spring systems for control of a movable link within a surgical device in accordance with an embodiment of the invention.

Use of the same reference symbols in different figures indicates similar or identical items.

DETAILED DESCRIPTION

Figure 2B:
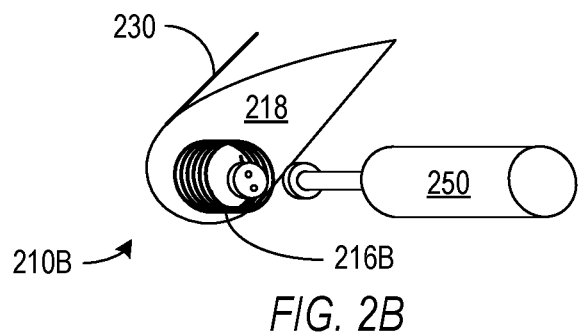
FIGS. 2B and 2C illustrate asymmetric spring systems in accordance with embodiments of the invention respectively using a torsion spring and a constant force spring to produce a tendon tension that remains constant with movement of the tendon but is adjustable through control mechanisms.

Compliance in an articulated surgical device such as a flexible entry guide is generally desirable to permit manual shaping of the device. In accordance with an aspect of the invention, tendons that connect to portions (e.g., mechanical links or vertebrae) in the flexible device to a backend mechanism are connected to spring systems that can accommodate manual manipulation of the flexible portion of the device without damaging the backend mechanism or connections of the tendons. In accordance with a further aspect of the invention, the spring system coupled to the drive tendons can be asymmetric or even a constant force spring, so that the spring system does not cause large reaction forces and the device does not rapidly spring back in response to external forces. The compliance of the surgical device and the lack of spring back may help to avoid tissue damage which might otherwise be caused during a surgical procedure when the flexible device could be subject to changing external forces.

FIG. 1 illustrates a flexible entry guide 100 in accordance with an embodiment of the invention. Entry guide 100 includes a flexible main tube 110 and a backend mechanism 120 at the proximal end of main tube 110. Main tube 110 is flexible in that main tube 110 can bend as needed to follow a convoluted path, but main tube 110 may include a series of rigid links or mechanical members that can act as articulated vertebrae to change the shape of main tube 110. Some exemplary articulated structures suitable for main tube 110 are described in U.S. Pat App. Pub. No. US 2007/0135803 A1, entitled "Methods and Apparatus for Performing Transluminal and Other Procedures" to Amir Belson; and U.S. Pat App. Pub. No. US 2004/0193009 A1, entitled "Endoscope having a Guide Tube" of Ross et al., which are hereby incorporated by reference in their entirety. Additionally, the articulated structure in an entry guide can employ some of the same architectures found in articulated wrists and similar robotic mechanism such as described in U.S. Pat. No. 6,817,974, entitled "Surgical Tool Having Positively Positionable Tendon-Actuated Multi-Disk Wrist Joint" to Cooper et al.; U.S. Pat. App. Pub. No. US 2004/0138700 A1, entitled "Flexible Wrist For Surgical Tool" of Cooper et al.; and U.S. Pat. No. 6,699,235, entitled "Platform Link Wrist Mechanism" to Wallace et al., which are hereby incorporated by reference in their entirety. A compliant sheath made from a rubber or plastic such as neoprene, pellethane, FEP, PTFE, Nylon, or similar material can cover the links and other internal structure of main tube 110 to provide a sealed enclosure for the internal mechanisms of the entry guide and to facilitate insertion and removal of main tube 110 during a surgical procedure. Main tube 110 would typically have a diameter between about 8 mm and about 25 mm, depending on the intended use of main tube 110 and the number of surgical instruments to be simultaneously guided. The overall length of main tube 110 can be selected according to the types of procedures being performed, but a typical length may be about 60 cm or more.

Main tube 110 also includes one or more instrument lumens 112. Each instrument lumen 112 can be a flexible tube made of rubber, neoprene, pellethane, FEP, PTFE, Nylon, or other flexible material. Each instrument lumen 112 runs most of the length of main tube 110 and generally passes through openings in or lies on surfaces of the links or members that are part of the mechanical system for controlling the shape of main tube 110. Each instrument lumen 112 can act to guide and house flexible surgical instruments that may be used during a surgical procedure. In particular, when needed, a flexible surgical instrument (not shown) can be inserted into an opening 112A at a proximal end of instrument lumen 112 and slid through the instrument lumen 112 so that a tool at the distal tip of the flexible surgical instrument emerges from an opening 112B at a distal end of the instrument lumen 112. Instrument lumens 112 would typically have diameters sized for standardized surgical instruments, e.g., 5 mm or 8 mm, so that an instrument lumen 112 can handle many different types of instruments, for example, various shapes and types of forceps, scissors, scalpels, and cauterizing instruments. When an instrument in an instrument lumen 112 is not currently needed, the instrument can be removed from that instrument lumen 112 and replaced by another flexible instrument without the need for a complex and time consuming steering process. Sensors and cameras or other vision systems could similarly be inserted through instrument lumens 112. Such easily replaceable instruments or other surgical systems may have their own backend mechanisms and/or interfaces that can be operated independently of backend mechanism 120. Alternatively or additionally, main tube 110 may include surgical instruments, sensors, vision systems, fluid channels, or other surgically useful systems (not shown) that are not intended to be removed during a surgical procedure, and such systems may be mechanically or electrically operated through an interface provided by backend mechanism 120.

Tendons 130 connect portions (e.g., mechanical links or fixed surgical systems) of main tube 110 to backend mechanism 120 and are shown in a cut-out portion of FIG. 1. Tendons 130 can be, for example, stranded or woven cables, monofilament lines, or tubes made of metal or a synthetic material that provides sufficient strength and flexibility for operation of the systems connected to tendons 130. Backend mechanism 120 generally operates as a transmission that pulls on tendons 130 when powered by a motor pack (not shown). Backend mechanism 120 includes an interface to which the motor pack can be mechanically coupled. In the illustrated embodiment, multiple toothed wheels 122 engage respective motors that rotate toothed wheels to control tensions in respective tendons 130 as described further below. For robotic operation, a control system (not shown) including a user interface operated by a surgeon and a computer executing software can control the motor pack. A sterile barrier may be provided between backend mechanism 120 and the main tube 110, so that the motor pack and any other systems connected to backend mechanism 120 are not contaminated during a surgical procedure.

FIG. 2A schematically illustrates a portion 200 of an entry guide using an asymmetric spring systems 210 in a backend mechanism 220 to control the respective tensions in tendons 230A and 230B coupled to a mechanical link 240. For ease of illustration, only two tendons 230A and 230B, generically referred to herein as tendons 230, are shown in FIG. 2A and the illustrated tendons 230 are attached to the same link 240. An actual entry guide may contain on the order of ten to in excess of one hundred links 240, and each link 240 may have one or more tendons 230 that terminate at that link 240. In general, the entry guide may be under-constrained, i.e., some links 240 may not be directly attached to or constrained by tendons 230, but may be displaced by the stiffness of a sheath or skin (not shown) around links 240 or by a stiffening rod extending through links 240. In an alternative embodiment, distal ends of tendons 230 may be attached to different portions of a flexible sheath to provide a continuum mechanism, which does not require links 240 or a hinged mechanism but is flexed by forces that tendons 230 apply to the sheath.

Tendons 230 may have proximal ends attached to respective asymmetric spring system 210 in backend mechanism 220 when compliance is desired in the attached link or mechanism of the entry guide. The entry guide may additionally include systems where compliance is not desired, and drive systems (not shown) in backend mechanism 220 may employ mechanisms, which are well known in the art, for non-compliant driving of tendons coupled the systems for which compliance is not desired.

Each spring system 210 in FIG. 2A includes a mechanical drive system 212, a spring 216, and a cam 218. Drive system 212 converts rotational motion of driver motors 250 into linear motion, and spring 216 connects to drive system 212 so that the linear motion of drive system 212 moves a proximal end of the spring 216. (Note that this conversion to linear motion is not a required element, the proximal end of each spring 216 may alternatively be attached to a cable that is wound around a pulley or capstan, which if necessary may be provided with a brake to prevent unwanted motion when the pulley or capstan is decoupled from a drive motor.) Cam 218 has a first guide surface on which a cable 217 attached to the distal end of spring 216 attaches and rides and a second guide surface on which a portion of tendon 230 attaches and rides. These surfaces of cam 218 are generally at different distances from a rotation axis of cam 218, so that the ratio of the tension in a tendon 230 to the spring force from spring 216 is equal to the ratio of the radial distance to the point where cable 217 separates from cam 218 to the radial distance to the point where tendon 230 separates from cam 218. Each surface of cam 218 may be a spiral surface that extends for multiple revolutions in order to provide the desired range of movement of the tendon 230.

The guide surfaces of cam 218 are further shaped to reduce or eliminate the dependency of the tension in attached tendon 230 on the position of the link 240 attached to that tendon 230, and to the shape of the path of the tendon between the cam 218 and the link 240. In particular, if cam 218 were replaced with a pulley having only circular guide surfaces, pulling tendon 230 would cause a proportional increase in the stretch of spring 216, and assuming that spring 212 obeys Hooke's law, a linear increase in the tension in the tendon 230. To reduce the dependence of the tension on external force applied to tendon 230 or link 240, one or both of the surfaces of cam 218 is not circular, but provides a variable moment arm upon which either the tension in tendon 230 or the force from spring 230 acts as cam 218 rotates. For example, rotation of cam 218 that tends to stretch spring 216 can either decrease the moment arm at which spring 216 acts on cam 218 or increase the moment arm on which the tension in tendon 230 acts. As is known for constant force springs, the shape of cam 218 can be selected so that the tension in tendon 230 remains constant as movement of tendon 230 causes rotation of cam 218, while at the same time, the spring force from spring 216 increases in accordance with Hooke's law. Spring system 210 can thus act as a constant force spring or alternatively just reduce the rate at which tension in tendon 230 changes as tendon 230 unwinds from cam 218.

Embodiments of cams and suitable systems for producing constant force springs using linear springs are described in more detail in U.S. Pat. App. Pub. No. US 2008/0277552 A1, entitled "Mechanical Arm Including a Counter-Balance" of Eugene F. Duvall and U.S. Pat. No. 7,428,855, entitled "Counter Balance System and Method with One or More Mechanical Arms" of Eugene F. Duval, which are hereby incorporated by reference in their entirety.

Each mechanical system 212 controls the position of the proximal end of the corresponding spring 216 and thereby influences the amount of stretch in the corresponding spring 216 and the tension in the attached tendon 230. In operation, if a mechanical system 212 in a spring system 210 pulls on the attached spring 216, the spring 216 begins to stretch, and if the link 240 and tendon 230 attached to the spring system 210 are held fixed, the force that spring 216 applies to cam 218 increases and therefore the tension in the attached cable 230 increases. Accordingly, the tension in a tendon 230 depends linearly (in accordance with Hooke's law, the moment arms of cam 218, and the spring constant of spring 216) on movement of the proximal end of spring 216, but each spring system 210 behaves asymmetrically, i.e., has a much weaker response or otherwise, acts with constant force, non-linear dependence, or smaller effective spring constant in response to external forces that move tendon 230.

Each drive system 212 as mentioned above converts rotational motion, which may be provided by a drive motor 250 mechanically coupled to the drive system 212, into linear motion of the proximal end of spring 216. In an exemplary embodiment, drive system 212 is a ball screw, which includes a threaded shaft 214 that provides a spiral raceway for ball bearings held within a bore of a ball nut 213. Ball nut 213 mechanically couples to a corresponding motor 250, so that as motor 250 turns, shaft 214 moves into or out of the bore of gear 213. A ball screw can provide minimal friction even when applying or withstanding significant force to or from spring 216. However, other mechanical systems could alternatively be employed to stretch spring 216. For example, a simple threaded device could operate in substantially the same manner as a ball screw but with greater friction. Alternatively, the proximal end of spring 216 could be attached to a cable that wraps around a capstan, so that a motor that drives the capstan could move the proximal end of spring 216. A system of gears and levers could also be used to convert rotational motion to linear motion, or instead of converting rotational motion, a linear drive system such as a solenoid could be used to move the proximal end of spring 216. The examples provided here simply illustrate a few of the mechanical systems suitable for drive system 212, but clearly many other mechanical systems could be employed to move the proximal end of spring 216.

An adjustable constant force spring or asymmetric spring system is not limited to use of linear or coils springs but can be constructed using other types of spring elements. FIG. 2B illustrates an example of a spring system 210B that uses a torsion spring 216B to produce a tension in a tendon 230 that is nearly independent of movement of tendon 230 but is adjustable using a drive motor 250. In system 210B, torsion spring 216B has a distal end attached to a cam 218 so that rotation of cam 218 changes the torsion in torsion spring 216B. The torque caused by torsion spring 216B on cam 218 thus varies (e.g., linearly) with the angle of rotation of cam 218. However, tendon 230 is wrapped on a surface of cam 218 that is shaped to change the moment arm on which tendon 230 acts so that a constant tension in tendon 230 causes a torque that changes in the same manner as torque from torsion spring 216B. As a result spring system 210B acts as a constant force spring. However, the spring force and tension in tendon 230 can be controlled by using motor 250 to rotate the proximal end of torsion spring 216B. In particular, motor 250 winding torsion spring 216B tighter (or looser) increases (or decreases) the tension in tendon 230. Accordingly, each spring system 216 of FIG. 2A can be replaced with a spring system 216B, provided that the difference in the direction of the interface between motors 250 and the spring systems 216 and 216B is accommodated.

Figure 2C:
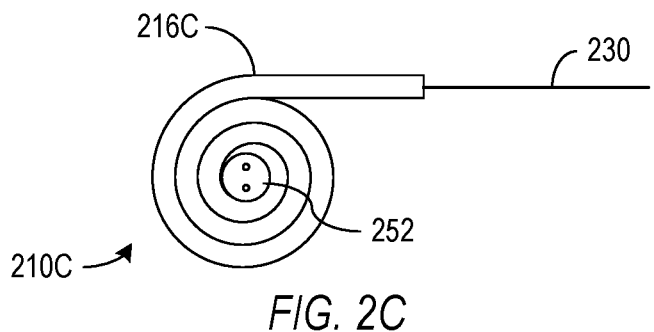

FIG. 2C shows another alternative asymmetric spring system 216C, which employs a constant force spring 216C. Constant-force spring 216C is a rolled ribbon of spring material that is relaxed when the ribbon is fully rolled up. As the ribbon unrolls, the portion of the ribbon near the roll produces the spring force. This spring force remains nearly constant as the ribbon unrolls because the portion of the ribbon that produces the spring force, i.e., the portion near the roll, has nearly the same shape as the spring unrolls. Tendon 230 when attached to a outer end of constant force spring 216C will experience a constant force from spring 216C as tendon 230 moves. However, an interface (e.g., a toothed wheel) 252 can be attached to the inner end of constant force spring 216C so that a motor (not shown) can engage interface 252 and change the constant force of spring 216C and the tension in tendon 250. Accordingly, each spring system 216 of FIG. 2A can be replaced with a spring system 216C.

FIG. 2A illustrates a configuration in which two tendons 230A and 230B are coupled to the same link 240. Link 240 can be mechanically constrained so that link 240 can only rotate about a single axis. Tendons 230A and 230B can then attach on the opposite side of the rotation axis, so that pulling on one tendon 230A or 230B causes one direction of rotation and pulling on the other tendon 230B or 230A cause rotation in the opposite direction. In this configuration, link 240 will be at rest when the forces, including external forces, frictional forces, and the tensions in tendons 230A and 230B, on link 240 are in equilibrium. A change in external forces applied to link 240, for example, by movement of a patient during insertion of the entry guide of FIG. 2A or after the entry guide has been inserted, can cause link 240 to move. Further, this movement will cause little or no change in the tension in tendons 230A and 230B since the spring systems 210 are relatively insensitive to movement of tendons 230A and 230B. The entry guide does not respond to the external forces with rapidly increasing resistance, and spring back, which might otherwise occur with a constant length positioning system. (In contrast, most robotic mechanics and controls are set up to hold a constant position with variable force, not a constant force with variable position as in the entry guide of FIG. 2A.) In the case where spring systems 210 act as constant force springs, the entry guide can be fully compliant without spring back even in the limit where friction is negligible. More generally, spring back can be avoided when increases in the tension in tendons 230 induced by the movement of the entry guide have less effect than does friction.

Link 240 in the entry guide of FIG. 2A can be moved by activating a motor 250 to turn a drive system 212 and change the tension in at least one of tendons 230A and 230B. The change in tension unbalances the equilibrium of forces causing link 240 to move until a new equilibrium is established. In general, this may involve operating one mechanical system 212 to stretch a corresponding spring 216 and increase tension in one tendon 230A or 230B. Optionally, the other mechanical system 210 may be operated to relax tension in the other tendon 230B or 230A. When link 240 rotates by the desired amount, tensions in the two tendons 230A and 230B can be adjusted as required to re-establish equilibrium (e.g., back to their original tension settings.) In general, the positions of links 240 do not have a fixed relation to the setting of mechanical systems 212. However, the position of each link 240 (or the shape of the entry guide as a whole) can be visually observed by an operator or sensed, for example, using a shape sensor such as described in U.S. Pat. App. Pub. No. US 2007/0156019 A1 (filed Jul. 20, 2006), entitled "Robotic Surgery System Including Position Sensors Using Fiber Bragg Gratings" by Larkin et al., and U.S. patent application Ser. No. 12/164,829 (filed Jun. 30, 2008) entitled "Fiber optic shape sensor" by Giuseppe M. Prisco, both of which are incorporated herein by reference. Movement of an entry guide employing the system of FIG. 2A may thus be robotically controlled or computer assisted using a control system 260 and a sensor 270 implementing a feedback loop that monitors the links 240 in the entry guide and controls drive motors 250, for example, to steer the entry guide during an insertion process. Steering an entry guide to follow a natural lumen generally does not require rapid or rigid response, so that slow movement and use of forces just above the external resistance and internal frictional force may be desired to minimize movement that overshoots target position.

Figure 3:
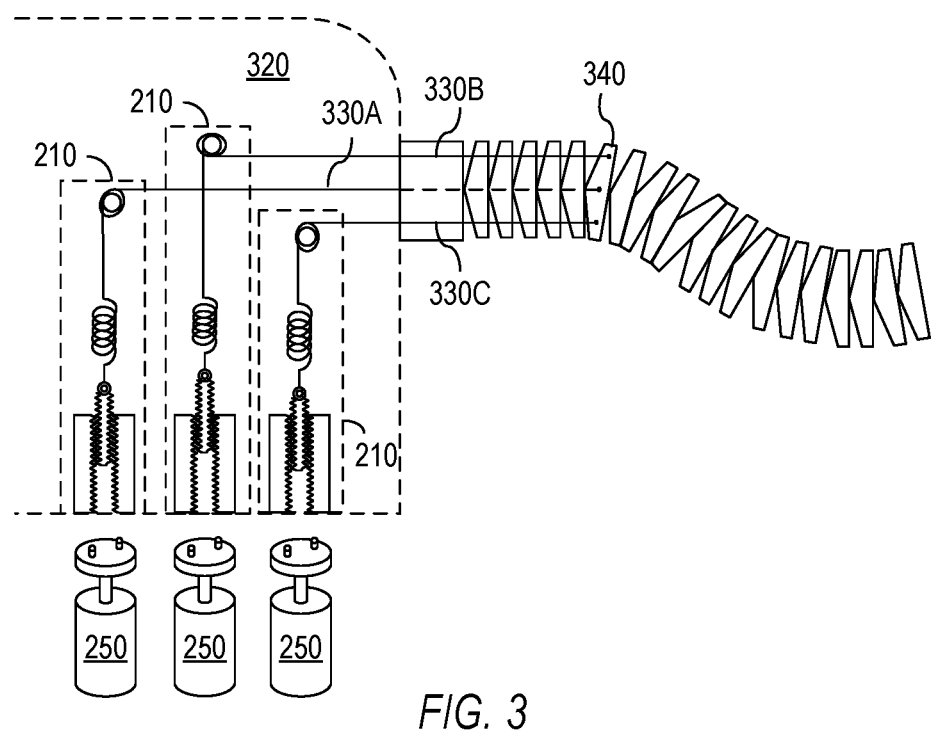
FIG. 3 illustrates connections of three tendons to asymmetric spring systems for control of a movable link within a surgical device in accordance with an embodiment of the invention.

FIG. 2A illustrates one specific configuration of backend mechanism 220 and spring systems 210 relative to a main tube of an entry guide. However, many other configurations can alternatively be employed. In particular, in FIG. 2A, the axis or rotation of gears 213 are substantially parallel to the direction from which the main tube of the entry guide extends from backend mechanism 220. If the spring systems 210B or 210C of FIG. 2B or 2C were used, the rotation axis of control motors 250 would be perpendicular to the direction of entry guide. FIG. 3 illustrates an alternative configuration using spring systems 210 but having a backend mechanism 320 using drive motors 250 with the rotation axes that are substantially perpendicular to the main tube. Again, spring systems 210B or 20C of FIG. 2B or 2C can be used in place of spring system 210 in the system of FIG. 3.

FIG. 3 also illustrates a configuration in which three tendons 330A, 330B, and 330C have distal ends attached to the same link 340. In this configuration, link 340 may have a pivot system that allows rotation of link 340 about two independent axes. The tensions in one or more of tendons 330A, 330B, and 330C can then be increased to tilt link 340 and the tensions can be brought back into balance (with each other, external forces, and friction) when link 340 reaches the desired orientation. The three tendons 330A, 330B, and 330C can thus be used to control two degrees of freedom of link 240.

Although the invention has been described with reference to particular embodiments, the description is only an example of the invention's application and should not be taken as a limitation. For example, although the above embodiments disclose specific embodiments of the invention that are entry guides, embodiments of the invention may also be suitable for use in other surgical instruments where compliance is desirable. Various other adaptations and combinations of features of the embodiments disclosed are within the scope of the invention as defined by the following claims.

What is claimed is:

1. A surgical device comprising:
   a shaft including a movable portion;
   a first tendon comprising a first end and a second end and extending from the first end of the first tendon to the second end of the first tendon, the first tendon extending through the shaft, and the second end of the first tendon being attached to the movable portion;
   a first asymmetric spring system comprising a first end and a second end, the first asymmetric spring system extending from the first end of the first asymmetric spring system to the second end of the first asymmetric spring system, wherein the first end of the first asymmetric spring system is attached to the first end of the first tendon, and wherein the first asymmetric spring system is configured such that a force applied by the first asymmetric spring system to the first tendon has greater dependence on a location of the second end of the first asymmetric spring system than on a location of the first end of the first asymmetric spring system; and
   a first mechanism connected to control the location of the second end of the first asymmetric spring system.

2. The device of claim 1, wherein the force applied by the first asymmetric spring system to the first tendon is independent of the location of the first end of the first asymmetric spring system and a location of the first tendon while the location of the second end of the first asymmetric spring system remains fixed.

3. The device of claim 1, wherein the shaft contains a lumen sized to guide a surgical instrument through the shaft.

4. The device of claim 1, wherein the shaft includes a plurality of members, each of which is articulated for control of a shape of the shaft.

5. The device of claim 1, further comprising:
a second tendon extending through the shaft and attaching to the movable portion of the shaft;
a second asymmetric spring system having a first end attached to the second tendon, wherein the second asymmetric spring system is such that a force applied by the second asymmetric spring system to the second tendon has greater dependence on a location of a second end of the second asymmetric spring system than on a location of the first end of the second asymmetric spring system; and
a second mechanism connected to control the location of the second end of the second asymmetric spring system.

6. The device of claim 5, further comprising:
a third tendon extending through the shaft and attaching to the movable portion of the shaft;
a third asymmetric spring system having a first end attached to the third tendon, wherein the third asymmetric spring system is such that a force applied by the third asymmetric spring system to the third tendon has greater dependence on a location of a second end of the third asymmetric spring system than on a location of the first end of the third asymmetric spring system; and
a third control mechanism connected to control the location of the second end of the third asymmetric spring system.

7. The device of claim 1, wherein the first asymmetric spring system comprises a spring element and a cam attached between the spring element and the first tendon.

8. The device of claim 7, wherein the first mechanism comprises a ball screw attached to the second end of the first asymmetric spring system.

9. The device of claim 1, further comprising:
a sensor in the shaft; and
a control system that operates the first mechanism to actuate the movable portion of the shaft until the sensor indicates the shaft has reached a desired configuration.

10. A surgical device comprising:
a shaft including a movable portion;
a first tendon comprising a first end and a second end and extending from the first end of the first tendon to the second end of the first tendon, the second end of the first tendon being attached to the movable portion of the shaft;
a first asymmetric spring system comprising a first end and a second end, the first asymmetric spring system extending from the first end of the first asymmetric spring system to the second end of the first asymmetric spring system, wherein the first end of the first asymmetric spring system is attached to the first end of the first tendon and is configured to apply a first force through the first tendon to the movable portion of the shaft, the first force having greater dependence on a location of the second end of the first asymmetric spring system than on a location of the first end of the first asymmetric spring system; and
a first mechanism connected to move the second end of the first asymmetric spring system so that a magnitude of the first force changes and the movable portion of the shaft moves.

11. The device of claim 10, wherein the shaft contains a lumen sized to guide a surgical instrument through the shaft.

12. The device of claim 11, wherein a portion of the lumen passes through the movable portion.

13. The device of claim 10, wherein the movable portion of the shaft includes a plurality of members, each of which is articulated for control of a shape of the shaft.

14. The device of claim 10, further comprising:
a second tendon attached to the movable portion of the shaft;
a second asymmetric spring system having a first end attached to the second tendon and applying a second force through the second tendon to the movable portion of the shaft, the second force having greater dependence on a location of a second end of the second asymmetric spring system than on a location of the first end of the second asymmetric spring system; and
a second mechanism connected to move the second end of the second asymmetric spring system so that a magnitude of the second force changes and the movable portion of the shaft moves.

15. The device of claim 14, further comprising:
a third tendon attached to the movable portion of the shaft;
a third asymmetric spring system having a first end attached to the third tendon and applying a third force through the third tendon to the movable portion of the shaft, the third force having greater dependence on a location of a second end of the third asymmetric spring system than on a location of the first end of the third asymmetric spring system; and
a third mechanism connected to move the second end of the third asymmetric spring system so that a magnitude of the third force changes and the movable portion of the shaft moves.

16. The device of claim 10, wherein the first asymmetric spring system comprises a cam and a spring element having a first end coupled to the cam, the cam being coupled to the first end of the spring element to apply the first force to the first tendon and being shaped such that a change in the magnitude of the first force as the movable portion of the shaft moves through a range of motion is less than a change in a magnitude of a force that the spring element applies to the cam.

17. The device of claim 16, wherein the first mechanism comprises a ball screw attached to a second end of the spring element, and the first mechanism alters the first asymmetric spring system by moving the second end of the first asymmetric spring system relative to the cam.

18. The device of claim 16, wherein the spring element comprises a linear spring attached to a cable that wraps around a portion of the cam.

19. The device of claim 16, wherein the spring element comprises a torsion spring attached to the cam.

20. The device of claim 10, further comprising:
a sensor in the shaft; and
a control system that operates the first mechanism to move the shaft until the sensor indicates the shaft has reached a desired configuration.

* * * * *